US008633342B2

(12) United States Patent
Vincent et al.

(10) Patent No.: US 8,633,342 B2
(45) Date of Patent: Jan. 21, 2014

(54) PROCESS FOR PRODUCING ALKYLAROMATIC COMPOUNDS

(75) Inventors: Matthew J. Vincent, Baytown, TX (US); Charles Morris Smith, Houston, TX (US)

(73) Assignee: Badger Licensing LLC, Boston, MA (US)

( * ) Notice: Subject to any disclaimer, the term of this patent is extended or adjusted under 35 U.S.C. 154(b) by 278 days.

(21) Appl. No.: 13/063,778

(22) PCT Filed: Sep. 24, 2009

(86) PCT No.: PCT/US2009/058248
§ 371 (c)(1),
(2), (4) Date: May 12, 2011

(87) PCT Pub. No.: WO2010/042327
PCT Pub. Date: Apr. 15, 2010

(65) Prior Publication Data
US 2011/0224468 A1   Sep. 15, 2011

Related U.S. Application Data

(60) Provisional application No. 61/104,447, filed on Oct. 10, 2008.

(30) Foreign Application Priority Data

Jan. 16, 2009   (EP) .................................... 09150689

(51) Int. Cl.
*C07C 2/66*   (2006.01)
*C07C 6/12*   (2006.01)

(52) U.S. Cl.
USPC ............ 585/323; 585/449; 585/467; 585/475

(58) Field of Classification Search
USPC .................................. 585/323, 467, 449, 475
See application file for complete search history.

(56) References Cited

U.S. PATENT DOCUMENTS 3,293,192 A   12/1966   Maher et al.
3,308,069 A   3/1967   Wadlinger et al.
(Continued)

FOREIGN PATENT DOCUMENTS

| EP | 0293032 | 7/1993 |
|---|---|---|
| EP | 0629549 | 12/1994 |
| EP | 0432814 | 6/1995 |
| WO | WO 97/17290 | 5/1997 |

*Primary Examiner* — Thuan D Dang
(74) *Attorney, Agent, or Firm* — Roberts Mlotkowski Safran & Cole, P.C.

(57) ABSTRACT

In a process for alkylation of an alkylatable aromatic compound to produce a monoalkylated aromatic compound, a first feed stream comprising fresh alkylatable aromatic compound is passed to a first reaction zone which comprises a transalkylation catalyst and which also receives a second feed stream comprising polyalkylated aromatic compounds. The first and second feed streams are contacted with the transalkylation catalyst in the first reaction zone under conditions to transalkylate the polyalkylated aromatic compounds with the alkylatable aromatic compound to produce the desired monoalkylated aromatic compound. A first effluent stream comprising unreacted alkylatable aromatic compound and the monoalkylated aromatic compound is removed from the first reaction zone and passed to a fractionation system to separate the first effluent stream into a first light fraction comprising the unreacted alkylatable aromatic compound and a first heavy fraction comprising the monoalkylated aromatic compound. At least part of one or more impurities in the fresh feed stream are removed in the first reaction zone.

16 Claims, 1 Drawing Sheet

(56) References Cited

U.S. PATENT DOCUMENTS

| | | |
|---|---|---|
| 3,442,795 A | 5/1969 | Kerr et al. |
| 3,449,070 A | 6/1969 | McDaniel et al. |
| 3,702,886 A | 11/1972 | Argauer et al. |
| 3,709,979 A | 1/1973 | Chu et al. |
| 3,751,504 A | 8/1973 | Keown et al. |
| 3,751,506 A | 8/1973 | Burress |
| 3,755,483 A | 8/1973 | Burress |
| 3,766,093 A | 10/1973 | Chu et al. |
| 3,832,449 A | 8/1974 | Rosinski et al. |
| RE28,341 E | 2/1975 | Wadlinger et al. |
| 3,894,104 A | 7/1975 | Chang et al. |
| 3,923,636 A | 12/1975 | Mead et al. |
| 3,972,983 A | 8/1976 | Ciric |
| 4,016,218 A | 4/1977 | Haag et al. |
| 4,076,842 A | 2/1978 | Plank et al. |
| RE29,948 E | 3/1979 | Dwyer et al. |
| 4,234,231 A | 11/1980 | Yan |
| 4,401,556 A | 8/1983 | Bezman et al. |
| 4,439,409 A | 3/1984 | Puppe et al. |
| 4,556,477 A | 12/1985 | Dwyer |
| 4,826,667 A | 5/1989 | Zones et al. |
| 4,891,458 A | 1/1990 | Innes et al. |
| 4,954,325 A | 9/1990 | Rubin et al. |
| 4,992,606 A | 2/1991 | Kushnerick et al. |
| 5,149,894 A | 9/1992 | Holtermann et al. |
| 5,236,575 A | 8/1993 | Bennett et al. |
| 5,250,277 A | 10/1993 | Kresge et al. |
| 5,258,565 A | 11/1993 | Kresge et al. |
| 5,362,697 A | 11/1994 | Fung et al. |
| 5,371,310 A | 12/1994 | Bennett et al. |
| 5,453,554 A | 9/1995 | Cheng et al. |
| 5,902,917 A | 5/1999 | Collins et al. |
| 6,077,498 A | 6/2000 | Diaz Cabañas et al. |
| 6,096,935 A * | 8/2000 | Schulz et al. ............ 585/323 |
| 6,231,751 B1 | 5/2001 | Canos et al. |
| 6,756,030 B1 | 6/2004 | Rohde et al. |
| 6,894,201 B1 | 5/2005 | Schmidt et al. |
| 6,995,295 B2 | 2/2006 | Clark et al. |
| 7,268,264 B2 | 9/2007 | Butler et al. |
| 2007/0179329 A1 | 8/2007 | Clark |

* cited by examiner

PROCESS FOR PRODUCING ALKYLAROMATIC COMPOUNDS

CROSS-REFERENCE TO RELATED APPLICATIONS

This application is a national stage filing of International Patent Cooperation Treaty Application No. PCT/US2009/058248 filed Sep. 24, 2009, which claims priority to U.S. Provisional Application Ser. No. 61/104,447, filed Oct. 10, 2008, and European Patent Application No. 09150689.9, filed Jan. 16, 2009, the contents of each are incorporated by reference in their entireties.

FIELD

The present invention relates to a process for producing alkylaromatic compounds, particularly ethylbenzene and cumene.

BACKGROUND

Ethylbenzene is a key raw material in the production of styrene and is produced by the reaction of ethylene and benzene in the presence of an acid catalyst. Similarly, cumene is an important precursor in the production of phenol and is produced by the alkylation of benzene with propylene in the presence of an acid catalyst.

Traditionally, ethylbenzene has been produced in vapor-phase reactor systems, in which the ethylation reaction of benzene with ethylene is carried out at a temperature of about 380-420° C. and a pressure of 150-250 psig in multiple fixed beds of zeolite catalyst. Ethylene exothermally reacts with benzene to form ethylbenzene, although undesirable chain and side reactions also occur. About 15% of the ethylbenzene formed further reacts with ethylene to form di-ethylbenzene isomers (DEB), tri-ethylbenzene isomers (TEB) and heavier aromatic products. All these chain reaction products are commonly referred as polyethylated benzenes (PEBs). In addition to the ethylation reactions, the formation of xylene isomers as trace products occurs by side reactions. This xylene formation in vapor phase processes may yield an ethylbenzene product with about 0.05-0.20 wt % of xylenes. The xylenes show up as an impurity in the subsequent styrene product, and are generally considered undesirable.

In order to minimize the formation of PEBs, a stoichiometric excess of benzene, about 400-2000% per pass, is applied, depending on process optimization. The effluent from the ethylation reactor contains about 70-85 wt % of unreacted benzene, about 12-20 wt % of ethylbenzene product and about 3-4 wt % of PEBs. To avoid a yield loss, the PEBs are converted back to ethylbenzene by transalkylation with additional benzene, normally in a separate transalkylation reactor.

By way of example, vapor phase ethylation of benzene over the crystalline aluminosilicate zeolite ZSM-5 is disclosed in U.S. Pat. No. 3,751,504 (Keown et al.), U.S. Pat. No. 3,751,506 (Burress), and U.S. Pat. No. 3,755,483 (Burress).

In recent years the trend in the industry has been to shift away from ethylbenzene vapor phase reactors to liquid phase reactors. Liquid phase reactors operate at a temperature of about 180-270° C., which is under the critical temperature of benzene (about 290° C.). One advantage of the liquid phase reactor is the very low formation of xylenes and other undesirable byproducts. The rate of the ethylation reaction is normally lower compared with the vapor phase, but the lower design temperature of the liquid phase reaction usually compensates economically for the negatives associated with the higher catalyst volume. In addition, the lower temperature liquid phase reaction enables a lower rate of the chain reactions that form PEBs; namely, about 5-8% of the ethylbenzene is converted to PEBs in liquid phase reactions versus the 15-20% converted in vapor phase reactions. Hence the stoichiometric excess of benzene in liquid phase systems is typically 150-400%, compared with 400-2000% in vapor phase.

Liquid phase ethylation of benzene using zeolite beta as the catalyst is disclosed in U.S. Pat. No. 4,891,458 and European Patent Publication Nos. 0432814 and 0629549. More recently it has been disclosed that MCM-22 and its structural analogues have utility in alkylation/transalkylation reactions, especially to produce ethylbenzene and cumene. See, for example, U.S. Pat. No. 4,992,606 (MCM-22), U.S. Pat. No. 5,258,565 (MCM-36), U.S. Pat. No. 5,371,310 (MCM-49), U.S. Pat. No. 5,453,554 (MCM-56), U.S. Pat. No. 5,149,894 (SSZ-25); U.S. Pat. No. 6,077,498 (ITQ-1); and U.S. Pat. No. 6,231,751 (ITQ-2).

Liquid phase aromatics alkylation plants offer significant advantages over vapor phase processes, because liquid phase processes operate at lower temperatures than their vapor phase counterparts. However, such liquid phase plants tend to be more sensitive to feed impurities which act as poisons to the zeolites used as alkylation and transalkylation catalysts. As a result most liquid phase processes require the use of high purity feedstocks and/or the provision of feed pretreatments to remove such feed impurities, particularly basic nitrogen compounds.

One known arrangement employed with liquid phase alkylation processes to remove feed impurities is the installation of a reactive guard bed located upstream of main alkylation reactor. The reactive guard bed incorporates one or more catalyst beds with the same or different catalysts, and it may be taken out of service at any time to replace catalyst, while the main alkylation unit continues to operate. In the reactive guard bed, the alkylatable aromatic compound and the alkylating agent are contacted in the presence of an alkylation catalyst prior to entry into the main alkylation reactor. The reactive guard bed not only serves to effect the desired alkylation reaction but also removes any reactive impurities in the feeds, such as nitrogen compounds, which could otherwise deactivate the remainder of the alkylation catalyst. The reactive guard bed catalysts are therefore subject to more frequent regeneration and/or replacement than the remainder of the alkylation catalyst. Also, the reactive guard bed is normally provided with a by-pass circuit so that the alkylation feedstocks can be fed directly to the alkylation reactor when the reactive guard bed is out of service. One example of an aromatics alkylation system including a reactive guard bed is disclosed in U.S. Pat. No. 6,995,295, the entire contents of which are incorporated herein by reference.

Although liquid phase alkylation processes produce much lower levels of polyalkylated species than vapor phase systems, process economics require the installation of a transalkylation reactor containing a transalkylation catalyst which converts polyalkylaromatic compounds in the presence of benzene to produce additional monoalkylated product. The benzene fed to the transalkylation reactor is typically a portion of the benzene recovered in the benzene column together with fresh make-up benzene, which is also fed to the column. All the remaining benzene recovered in the benzene column is fed through the reactive guard bed to the alkylation catalyst.

According to the present invention, an improved aromatics alkylation process has been developed in which the transalkylation reactor containing a transalkylation catalyst receives substantially all of the fresh make-up benzene, as compared to merely a slip stream from the benzene column overhead. Feeding all the make-up benzene to the transalkylation reactor allows the transalkylation reactor to be used as a reactive guard bed for removing impurities from the benzene feed. Also, it enables a much higher molar ratio of benzene to polyalkylated aromatic compounds to be maintained in the transalkylation reactor. This results in reduced polyalkylated aromatic by-product make, a higher per pass conversion of polyalkylated aromatic compounds and a higher thermodynamic yield of the desired monoalkylated product. With a higher per pass conversion of polyalkylated aromatic compounds, the recycle flow rates diminish and the amount of polyalkylated aromatic by-products requiring distillation also diminishes. Overall, energy costs are therefore reduced. In addition, the transalkylation reaction is thermo-neutral allowing the entire unit to be operated at relatively low temperatures. The transalkylation catalyst in the transalkylation reactor is generally a zeolite with higher aluminum content and a larger pore size than the alkylation catalyst. This greatly enhances the effectiveness of the transalkylation catalyst in reducing benzene feed impurities.

U.S. Pat. No. 5,902,917 discloses a process for producing alkylaromatic compounds, especially ethylbenzene and cumene, wherein a feedstock is first fed to a transalkylation zone and the entire effluent from the transalkylation zone is then cascaded directly into an alkylation zone along with an olefin alkylating agent, especially ethylene or propylene. However, the fresh make-up benzene is fed directly to the alkylation zone and there is no suggestion of using the transalkylation zone as a reactive guard bed.

In the improved process, the desired monoalkylated product is recovered from the effluents from the transalkylation and alkylation reactors and the unreacted alkylatable aromatic is fed to the alkylation reactor. In this way, loss of monoalkylated product to, for example, additional polyalkylated species in the alkylation reactor is avoided.

U.S. Pat. No. 6,096,935 discloses a process for producing alkylaromatic compounds using a transalkylation reaction zone and an alkylation reaction zone, wherein the transalkylation reaction zone effluent is passed to the alkylation reaction zone where aromatic compounds in the transalkylation reaction zone effluent are alkylated to the desired alkylaromatic compounds, particularly ethylbenzene and cumene. Again, there is no suggestion of using the transalkylation zone as a reactive guard bed and, although at least part of the fresh make-up benzene is fed to the transalkylation reaction zone, the entire effluent from the transalkylation zone is cascaded directly into the alkylation zone.

U.S. Patent Application Publication No. 2007/0179329 discloses an aromatics alkylation process in which the alkylatable aromatic compounds, and optionally at least part of the alkylating agent, are passed through a reactive guard bed and in the presence of a certain amount of water, containing alkylation or transalkylation catalyst, prior to entry into the alkylation zone.

U.S. Pat. No. 6,894,201 discloses a process and apparatus for removing nitrogen compounds from an alkylation substrate such as benzene. A conventional adsorbent bed containing clay or resin is used to adsorb basic organic nitrogen compounds, whereas a hot adsorbent bed of acidic molecular sieve is used to adsorb the weakly basic nitrogen compounds, such as nitrites, generally in the presence of water. The hot adsorbent bed can be provided in the transalkylation reactor upstream of the transalkylation catalyst (FIG. 6), in the alkylation reactor upstream of the alkylation catalyst (FIG. 7) or both (FIG. 8).

SUMMARY

In one aspect, the present invention relates to a process for alkylation of an alkylatable aromatic compound to produce a monoalkylated aromatic compound, the process comprising:

(a) passing a first feed stream comprising fresh alkylatable aromatic compound to a first reaction zone comprising a transalkylation catalyst;

(b) passing a second feed stream comprising polyalkylated aromatic compounds to said first reaction zone;

(c) contacting said first and second feed streams with said transalkylation catalyst in said first reaction zone under conditions to transalkylate said polyalkylated aromatic compounds with said alkylatable aromatic compound to produce said monoalkylated aromatic compound;

(d) removing from said first reaction zone a first effluent stream comprising unreacted alkylatable aromatic compound and said monoalkylated aromatic compound;

(e) passing said first effluent stream to a fractionation system to separate said first effluent stream into a first light fraction comprising said unreacted alkylatable aromatic compound and a first heavy fraction comprising said monoalkylated aromatic compound;

(f) recovering monoalkylated aromatic compound from said first heavy fraction;

(g) passing said first light fraction comprising said alkylatable aromatic compound and a third feed stream comprising an alkylating agent to a second reaction zone comprising an alkylation catalyst;

(h) contacting said first light fraction and third feed stream with said alkylation catalyst in said second reaction zone under conditions to alkylate said alkylatable aromatic compound with said alkylating agent and produce a second effluent stream comprising said monoalkylated aromatic compound; and (i) recovering monoalkylated aromatic compound from said second effluent stream.

In some embodiments, the first feed stream comprising one or more feed impurities. At least part of said feed impurities are removed in said first reaction zone in contacting step (c).

In some embodiments, the feed impurities in said first feed stream comprise at least 0.02 ppm, preferably at least 0.005 ppm by weight of said first feed stream. Such feed impurities are selected from the group consisting of compounds having one or more of the following elements: halogens, oxygen, sulfur, arsenic, selenium, tellurium, phosphorus and Group 1 through Group 12 metals. Typically, said feed impurities include reactive nitrogen compounds, other than molecular nitrogen. The transalkylation catalyst acts as a guard bed to remove at least 10 wt % of said reactive nitrogen compounds in said first feed stream.

Conveniently, the process further comprises:

(j) passing said second effluent stream to a fractionation system to separate said second effluent stream into a second light fraction comprising unreacted alkylatable aromatic compound and a second heavy fraction comprising said monoalkylated aromatic compound and polyalkylated aromatic compounds, said monoalkylated aromatic compound being recovered in (h) from said second heavy fraction.

Conveniently, said second light fraction comprising unreacted alkylatable aromatic compound is passed to said second reaction zone.

In one embodiment, said first effluent stream and said second effluent stream are passed to the same fractionation system.

Conveniently, the process further comprises:

(k) passing said first and second heavy fractions to at least one further fractionation system to recover said monoalkylated aromatic compound from said combined fractions and separate a third fraction comprising said polyalkylated aromatic compounds; and (l) recycling at least part of said third fraction to said first reaction zone.

In one embodiment, the process further comprises effecting the following steps on an intermittent basis:

(m) ceasing passage of said first and second feed streams to said first reaction zone;

(n) passing said first and second feed streams to a third reaction zone comprising a transalkylation catalyst;

(o) contacting said first and second feed streams with said transalkylation catalyst in said third reaction zone under conditions to remove at least part of said feed impurities in said first feed stream and to transalkylate said polyalkylated aromatic compounds with said alkylatable aromatic compound to produce said monoalkylated aromatic compound; and (p) replacing or regenerating the transalkylation catalyst in said first reaction zone.

Conveniently, the transalkylation catalyst and the alkylation catalyst comprise aluminosilicate molecular sieves wherein the transalkylation catalyst has silica to alumina molar ratio less than that of the alkylation catalyst.

Conveniently, the transalkylation catalyst and the alkylation catalyst comprise different aluminosilicate molecular sieves wherein the transalkylation catalyst has a pore size greater than that of the alkylation catalyst.

Conveniently, said transalkylation catalyst comprises a molecular sieve having a Constraint Index less than 2. Typically, the transalkylation catalyst comprises a molecular sieve selected from the group consisting of zeolite beta, zeolite Y, Ultrastable Y (USY), Dealuminized Y (Deal Y), Rare Earth Y (REY), mordenite, ZSM-3, ZSM-4, ZSM-18, ZSM-20, and mixtures thereof.

Conveniently, said transalkylation catalyst and/or said alkylation catalyst comprises a molecular sieve selected from the group consisting of zeolite beta, a molecular sieve having a Constraint Index of about 2 to about 12, and a molecular sieve of the MCM-22 family. Typically, the alkylation catalyst comprises a molecular sieve of the MCM-22 family selected from the group consisting of MCM-22, PSH-3, SSZ-25, ERB-1, ITQ-1, ITQ-2, ITQ-30, MCM-36, MCM-49, MCM-56, UZM-8 and mixtures thereof.

In one embodiment, the conditions in said first reaction zone during said contacting (c) are such as to maintain said polyalkylated aromatic compound and said alkylatable aromatic compound substantially in the liquid phase, and conveniently comprise a temperature between about 50° C. and about 300° C. and a pressure between about 170 kPa and about 10,000 kPa.

In one embodiment, the conditions in said second reaction zone during said contacting (h) are such as to maintain said alkylatable aromatic compound substantially in the liquid phase, and conveniently comprise a temperature between about 50° C. and about 270° C. and a pressure between about 1,000 kPa and about 10,000 kPa.

In one embodiment, the alkylatable aromatic compound comprises benzene or naphthalene and the alkylating agent comprises at least one of ethylene, propylene, 1-butene, 2-butene, and isobutylene.

DETAILED DESCRIPTION OF THE EMBODIMENTS

Figure 1:
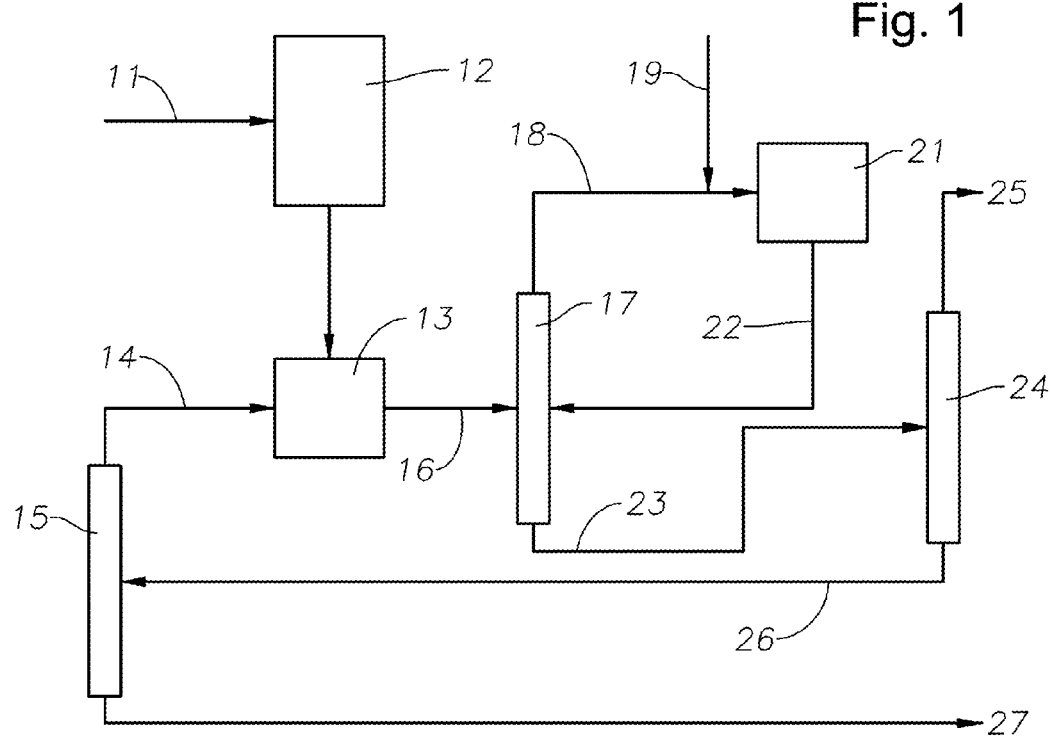
FIG. 1 is a simplified flow diagram of a process for producing monoalkyl aromatic compounds, such as ethylbenzene, according to one embodiment of the present invention.

Described herein is a process for producing monoalkylaromatic compounds by alkylation of an alkylatable aromatic compound with an alkylating agent in the presence of an alkylation catalyst followed by transalkylation of any polyalkylated aromatic compounds generated in the alkylation step with further alkylatable aromatic compound to produce additional monoalkylaromatic product. The transalkylation step is conducted in the presence of a separate transalkylation catalyst and, in the present process, the fresh feed containing the alkylatable aromatic is initially contacted with the transalkylation catalyst so that the latter acts not only to transalkylate the polyalkylated aromatic compounds to produce additional monoalkylaromatic product but also acts as a reactive guard bed to remove impurities, such as reactive nitrogen compounds, contained in the alkylatable aromatic feed. Since the transalkylation catalyst may be chosen to have more Bronsted acid sites per unit weight and a larger pore size than the alkylation catalyst, it is better suited than the alkylation catalyst to act as a guard bed for removing poisons.

In addition, feeding all the fresh aromatic feed to the transalkylation catalyst allows a much higher molar ratio of aromatic substrate to polyalkylated aromatic compounds to be maintained in the transalkylation step. This allows for reduced by-product make, a higher per pass conversion and a higher thermodynamic yield of the desired monoalkylated product. In turn a higher per pass conversion of polyalkylated aromatic compounds reduces both recycle rates and the amounts of by-products requiring distillation, thereby lowering energy costs. In addition, the transalkylation reaction is thermo-neutral allowing the entire unit to be operated at relatively low temperatures.

As used herein, the term "reactive nitrogen compounds" means nitrogen compounds other than molecular nitrogen, which is relatively inert under the conditions employed in the present process.

Feedstocks

The feedstocks used in the present process include an alkylatable aromatic compound and an alkylating agent.

The term "aromatic" in reference to the alkylatable compounds which are useful herein is to be understood in accordance with its art-recognized scope to include both mono- and polynuclear aromatic hydrocarbons. Compounds of an aromatic character which possess a heteroatom are also useful provided they do not act as catalyst poisons under the reaction conditions selected.

Suitable aromatic hydrocarbons include benzene, naphthalene, anthracene, naphthacene, perylene, coronene, and phenanthrene, with benzene being preferred.

Generally, the fresh aromatic feedstock employed in the present process will contain feed impurities which, if not removed, will be deleterious to the alkylation and/or transalkylation catalyst. Examples of such feed impurities include reactive nitrogen compounds, halogens and/or compounds comprising one or more of oxygen, sulfur, arsenic, selenium, tellurium, phosphorus and metals, including metals in Group 1 to Group 12 of the periodic chart of elements. Typically, these feed impurities are present in commercially available feedstocks in amounts that are not detectable by conventional analytical means. In such cases, the removal of the non-detectable feed impurities is evidenced by a recovery of catalyst activity and product conversion following treatment.

In some embodiments, the feed impurities are present in such feedstocks in amounts of at least 0.02 ppm by weight (wppm), often from at least 1 wppm to 5 wppm, even 5 wppm or more. In addition, as supplied, most commercial aromatic feeds are water saturated, that is they contain at least 50 wppm, generally at least 200 wppm, water. The present process provides an advantageous method of reducing the amounts of theses feed impurities in commercial aromatic feedstocks to acceptable levels.

The alkylating agents which are useful in the present process generally include any organic compound having at least one available alkylating group capable of reaction with the alkylatable aromatic compound, the alkylating group typically possessing from 1 to 5 carbon atoms. Examples of suitable alkylating agents are olefins such as ethylene, propylene, the butenes and the pentenes; alcohols (inclusive of monoalcohols, dialcohols, trialcohols, etc.) such as methanol, ethanol, the propanols, the butanols and the pentanols; aldehydes such as formaldehyde, acetaldehyde, propionaldehyde, butyraldehyde and n-valeraldehyde; and, alkyl halides such as methyl chloride, ethyl chloride, the propyl chlorides, the butyl chlorides and the pentyl chlorides, and so forth.

Preferably, the feedstocks in the present process are benzene and ethylene and the desired reaction product is ethylbenzene.

Alkylation Reaction

The primary step in the alkylation reaction involves contacting the alkylatable aromatic compound with an alkylating agent in the presence of an alkylation catalyst under conditions such that the alkylating agent reacts with the alkylatable aromatic compound to selectively produce the desired monoalkylaromatic compound. Although the alkylation reaction can occur in the vapor phase, it is generally desirable to control the alkylation conditions so as to maintain the alkylatable aromatic compound substantially in the liquid phase. For example, where the alkylatable aromatic compound includes benzene, the alkene includes ethylene and the alkylaromatic compound includes ethylbenzene, the alkylation conditions conveniently comprise a temperature between about 50° C. and about 270° C. and a pressure between about 1,000 kPa and about 10,000 kPa.

In one embodiment, the alkylation catalyst comprises at least one medium pore molecular sieve having a Constraint Index of 2-12 (as defined in U.S. Pat. No. 4,016,218). Suitable medium pore molecular sieves include ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231.

In another embodiment, the alkylation catalyst comprises at least one molecular sieve of the MCM-22 family. As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof.

In a further embodiment, the alkylation catalyst comprises one or more large pore molecular sieves having a Constraint Index less than 2. Suitable large pore molecular sieves include zeolite beta, zeolite Y, Ultrastable Y (USY), Dealuminized Y (DealY), mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite Beta is described in U.S. Pat. Nos. 3,308,069, and Re. No. 28,341. Low sodium Ultrastable Y molecular sieve (USY) is described in U.S. Pat. Nos. 3,293,192 and 3,449,070. Dealuminized Y zeolite (DealY) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

Preferred molecular sieves for the alkylation reaction comprise zeolite beta, ZSM-5, and molecular sieves of the MCM-22 family.

The above molecular sieves may be used as the alkylation catalyst without any binder or matrix, i.e., in so-called self-bound form. Alternatively, the molecular sieve may be composited with another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 percent by weight and more usually, particularly, when the composite is prepared in the form of beads, in the range of about 2 to about 80 weight percent of the composite.

The alkylation catalyst can be provided as a single catalyst bed, normally a fixed bed, in an alkylation reactor. However, to enhance the monoselectivity of the reaction, the alkylation catalyst is normally divided into a plurality of series-connected catalysts beds, with substantially all the alkylatable aromatic compound being fed to the first catalyst bed and the alkylating agent feed being split between the beds.

Transalkylation Reaction

The effluent from the alkylation reaction will inevitably contain some polyalkylated aromatic compounds, in addition to the desired monoalkylated product and unreacted alkylatable aromatic compound. Thus, the alkylation effluent is passed to a product separation system, normally a series of distillation columns, which not only serves to remove unreacted alkylated aromatic compound, and desired monoalkylated product, but also separates the polyalkylated species. In the primary step of the transalkylation reaction, the polyalkylated species are then fed to a transalkylation reactor, which is separate from the alkylation reactor, where additional monoalkylated product is produced by reacting the polyalkylated species with additional aromatic compound in the presence of a transalkylation catalyst. Typically, the transalkylation reactor is operated under conditions such that the polyalkylated aromatic compounds and the alkylatable aromatic compound are at least predominantly in the liquid phase.

For example, suitable conditions for carrying out the liquid phase transalkylation of benzene with polyethylbenzenes may include a temperature of from about 150° C. to about 260° C., a pressure of 7000 kPa or less, a WHSV based on the weight of the total liquid feed to the reaction zone of from about 0.5 to about 100 hr$^{-1}$ and a mole ratio of benzene to polyethylbenzene of from about 1:1 to about 30:1.

The transalkylation catalyst can comprise one or more of any of the molecular sieves discussed above in relation to the alkylation catalyst, such as MCM-22 family material, and can be used with or without a binder or matrix. Normally, however, although both the transalkylation catalyst and the alkylation catalyst comprise aluminosilicate molecular sieves, the transalkylation catalyst has silica to alumina molar ratio less than that of the alkylation catalyst. In addition, the transalkylation catalyst normally employs a molecular sieve having a pore size greater than that of the alkylation catalyst Generally, the transalkylation catalyst comprises a molecular sieve having a Constraint Index less than 2, particularly a molecular sieve selected from the group consisting of zeolite beta, zeolite Y, Ultrastable Y (USY), Dealuminized Y (DealY), Rare Earth Y (REY), mordenite, ZSM-3, ZSM-4, ZSM-5, ZSM-11, ZSM-18, ZSM-20, and mixtures thereof.

Feedstock Treatment

As discussed above, the fresh alkylatable aromatic feedstock employed in the present process will normally contain significant quantities of catalyst poisons, particularly reactive nitrogen compounds and non-reactive nitrogen compounds, as well as water. Typically, therefore, the aromatic feedstock is subjected to a pretreatment step to reduce its water content and to remove at least some of the catalyst poisons. Such pretreatment normally involves passing the alkylatable aromatic feedstock through a dehydration zone, such as a lights removal unit, before or after a bed of an adsorbent, such as a clay, a resin or a molecular sieve, generally at or near ambient conditions, such from as a temperature of about 25° C. to about 250° C., preferably from about 25° C. to about 150° C., and a pressure of about 50 to about 10,000 kPa.

Next, the alkylatable aromatic feedstock is passed through a factionation column to separate a water phase and hydrocarbon phase in the overhead stream. A dry aromatic feedstock is separated in the bottoms stream which comains no more than 100 ppm of water. It is found that some of the catalyst poisons are removed from system with the water phase.

However, whereas adsorptive pretreatment and fractionation are effective to remove many of the deleterious impurities in the alkylatable aromatic feedstock, it is found that, even after such pretreatment, the impurity levels, particularly of reactive nitrogen compounds, are sufficiently high albeit in some instances undetectable to result in significant reduction in catalyst life, particularly of the alkylation catalyst, if the aromatic feedstock is allowed to contact the catalyst without further treatment. Thus, in the present process, the entire fresh alkylatable aromatic feedstock, either with or without, adsorptive pretreatment, is fed to the transalkylation catalyst so that the latter acts not only to facilitate conversion of the polyalkylated aromatic by-products into additional monoalkylated product but also acts as a reactive guard bed to further reduce the level of impurities in the feedstock, typically by at least 10%, such as by at least 20%, for example by at least 30%.

The use of the transalkylation catalyst as a reactive guard bed necessarily results in some poisoning of the transalkylation catalyst but, since the transalkylation catalyst may be chosen to have a lower silica to alumina molar ratio and a larger pore size than the alkylation catalyst, it is generally more effective as a guard bed than, for example, known arrangements that employ a bed of alkylation catalyst as the guard bed. Moreover, feeding all the fresh make-up benzene to the transalkylation catalyst allows a much higher molar ratio of benzene to polyalkylated aromatic compounds to be maintained in the transalkylation unit. This allows for reduced by-product make, a higher per pass conversion and a higher thermodynamic yield of the desired monoalkylated product. With a higher per pass conversion of polyalkylated aromatic compounds, the recycle rates diminish and the amount of by-products requiring distillation also diminishes. Overall, energy costs are therefore reduced. Typically, in the present process, the molar ratio of benzene to polyalkylated aromatic compounds fed to the transalkylation reactor is at least 1:1, such as between about 1:1 and about 30:1; 1:1 and 15:1; and 1:1 and 10:1.

In one embodiment, the process employs two separate beds of transalkylation catalyst each switchable intermittently between an operative mode, in which the catalyst bed is functioning as a transalkylator and reactive guard bed, and an inoperative mode, in which the catalyst is being regenerated or replaced. In this way, one bed will always be in the operative mode, while the other bed is in the inoperative mode. Also, these beds may be operated in series or in parallel.

One embodiment of the present process, in which the alkylatable aromatic compound is benzene and the alkylating agent is a dilute ethylene stream, is shown in FIG. 1.

Referring to FIG. 1, fresh benzene feed having impurities, such as nitrogen impurities, is supplied through line 11 and passed to an adsorption unit 12 which contains molecular sieve absorbents and/or other treatment materials, including, for example, clay and/or resins, to remove at least a portion of the feed impurities. The treated fresh benzene feed is passed to a transalkylation reactor 13, which also receives polyethylbenzenes (PEBs) as an overhead steam 14 from a PEB distillation column 15. The transalkylation reactor 13 contains one or more beds of transalkylation catalyst, such as zeolite beta, zeolite Y, Ultrastable Y (USY), Dealuminized Y (Deal Y), Rare Earth Y (REY), mordenite, ZSM-3, ZSM-4, ZSM-18, ZSM-20, and mixtures thereof, and is operated under conditions such that the benzene and PEBs are predominantly in the liquid phase and react together to produce ethylbenzene (EB). The transalkylation reactor 13 also acts as a guard bed to remove at least part of the reactive nitrogen impurities and other impurities in the fresh benzene feed.

The effluent from transalkylation reactor 13 is composed mainly of unreacted benzene having a reduced amount of impurities, EB product, PEBs and heavy compounds, exiting the reactor 13 through line 16. The effluent in line 16 is fed to a benzene distillation column 17 where the unreacted benzene is separated from the effluent as an overhead steam 18. The benzene stream 18 is then fed, together with an ethylene feed stream 19, to an alkylation reactor 21 containing a plurality of series-connected beds of alkylation catalyst, such as an MCM-22 family zeolite. The alkylation reactor is operated under conditions such that the benzene is predominantly in the liquid phase and reacts with the ethylene feed to produce EB, together with some PEBs.

The effluent from alkylation reactor 21 is composed mainly of unreacted benzene, EB product and some PEBs. The alkylation effluent exits the reactor 21 through line 22 and is fed to the benzene distillation column 17. The unreacted benzene is removed form the alkylation effluent in the column 17 and passes as part of the overhead stream 18 back to the reactor 21, leaving a bottoms stream 23 composed mainly of EB product and PEBs. The bottoms stream is passed to an EB distillation column 24, where the EB product is recovered as overhead 25, while the bottoms stream 26 is fed to the PEB column 15. In the PEB column 15, the PEBs are removed as overhead steam 14 from the heavies, which are discarded as waste stream 27.

Figure 2:
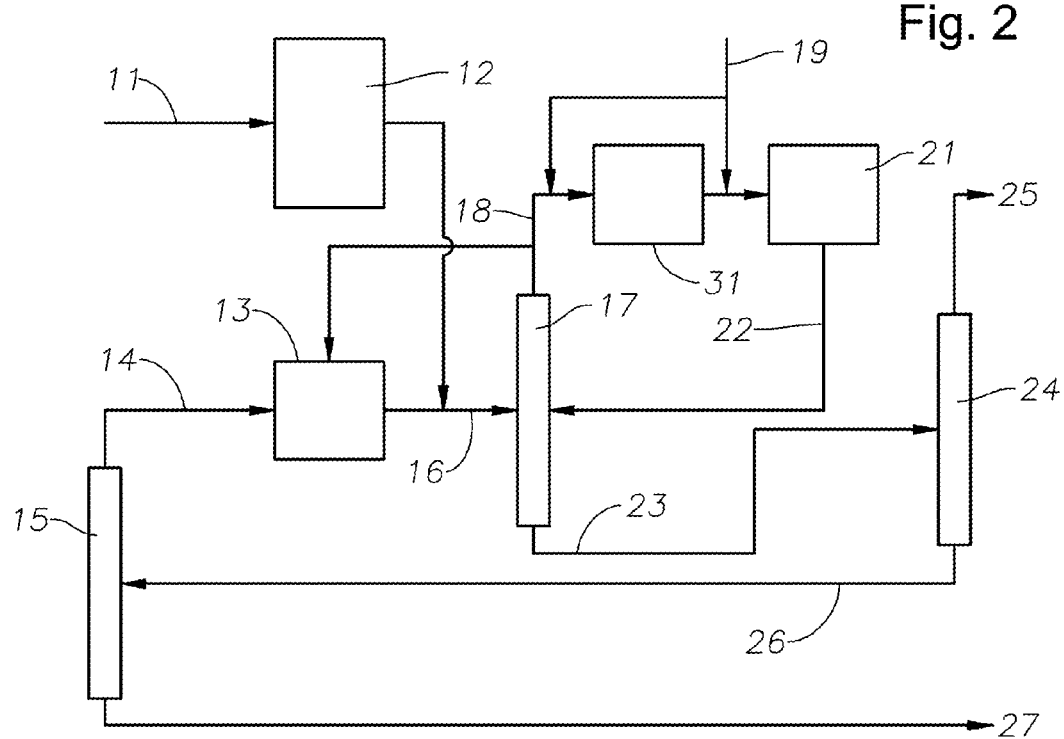
FIG. 2 is a flow diagram of a prior art process for producing ethylbenzene.

In contrast, a typical prior art process for producing EB is shown in FIG. 2, wherein like numerals are employed to indicate common components with the embodiment of FIG. 1. Thus in FIG. 2, the fresh benzene stream 11, after passage through the adsorption unit 12 and untreated effluent 16 from the transalkylation unit are fed to the benzene column 17. Part of the benzene overhead stream 18, which still contains feed impurities (i.e., reactive nitrogen impurities and other impurities), is fed to a reactive guard bed 31 containing alkylation catalyst. The remainder of the benzene overhead from the benzene column 17 is fed as a slip stream 32 to the transalkylation reactor 13.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for alkylation of an alkylatable aromatic compound to produce a monoalkylated aromatic compound, the process comprising:
   (a) passing a first feed stream comprising all of fresh alkylatable aromatic compound and one or more impurities including reactive nitrogen compounds to a first reaction zone comprising a transalkylation catalyst;
   (b) passing a second feed stream comprising polyalkylated aromatic compounds to said first reaction zone;
   (c) contacting said first and second feed streams with said transalkylation catalyst in said first reaction zone under conditions to transalkylate said polyalkylated aromatic compounds with said alkylatable aromatic compound to produce said monoalkylated aromatic compound, and to remove at least 10% of said reactive nitrogen compound impurities;
   (d) removing from said first reaction zone a first effluent stream comprising unreacted alkylatable aromatic compound and said monoalkylated aromatic compound;
   (e) passing said first effluent stream to a fractionation system to separate said first effluent stream into a first light fraction comprising said unreacted alkylatable aromatic compound and a first heavy fraction comprising said monoalkylated aromatic compound;
   (f) recovering monoalkylated aromatic compound from said first heavy fraction;
   (g) passing said first light fraction comprising said alkylatable aromatic compound and a third feed stream comprising an alkylating agent to a second reaction zone comprising an alkylation catalyst;
   (h) contacting said first light fraction and third feed stream with said alkylation catalyst in said second reaction zone under conditions to alkylate said alkylatable aromatic compound with said alkylating agent and produce a second effluent stream comprising said monoalkylated aromatic compound, unreacted alkylatable aromatic compounds and polyalkylated aromatic compounds; and
   (i) recovering monoalkylated aromatic compound from said second effluent stream,
   wherein the transalkylation catalyst and the alkylation catalyst comprise aluminosilicate molecular sieves wherein the transalkylation catalyst has silica to alumina molar ratio less than that of the alkylation catalyst,
   said transalkylation catalyst comprises a molecular sieve having a Constraint Index less than 2 selected from the group consisting of zeolite beta, zeolite Y, Ultrastable Y (USY), Dealuminized Y (Deal Y), mordenite, ZSM-3, ZSM-4, ZSM-18, and ZSM-20, and said alkylation catalyst comprises a molecular sieve selected from the group consisting of zeolite beta, a molecular sieve having a Constraint Index of about 2 to about 12, and a molecular sieve of the MCM-22 family.

2. The process of claim 1, wherein said feed impurities in said first feed stream comprise at least 0.02 ppm by weight of said first feed stream.

3. The process of claim 1, wherein said feed impurities in said first feed stream additionally comprise compounds having one or more of the following elements: halogens, oxygen, sulfur, arsenic, selenium, tellurium, phosphorus and Group 1 thru Group 12 metals.

4. The process of claim 1 and further comprising:
(j) passing said second effluent stream to a fractionation system to separate said second effluent stream into a second light fraction comprising unreacted alkylatable aromatic compound and a second heavy fraction comprising said monoalkylated aromatic compound and polyalkylated aromatic compounds, said monoalkylated aromatic compound being recovered in (h) from said second heavy fraction.

5. The process of claim 4, wherein said second light fraction comprising unreacted alkylatable aromatic compound is passed to said second reaction zone.

6. The process of claim 4, wherein said first effluent stream and said second effluent stream are passed to the same fractionation system.

7. The process of claim 4 and further comprising the steps of:
(k) passing said first and second heavy fractions to at least one further fractionation system to recover said monoalkylated aromatic compound from said combined fractions and separate a third fraction comprising said polyalkylated aromatic compounds; and
(l) recycling at least part of said third fraction to said first reaction zone.

8. The process of claim 1 and further comprising the steps on an intermittent basis:
(m) ceasing passage of said first and second feed streams to said first reaction zone;
(n) passing said first and second feed streams to a third reaction zone comprising a transalkylation catalyst;
(o) contacting said first and second feed streams with said transalkylation catalyst in said third reaction zone under conditions to remove at least part of said feed impurities in said first feed stream and to transalkylate said polyalkylated aromatic compounds with said alkylatable aromatic compound to produce said monoalkylated aromatic compound; and
(p) replacing or regenerating the transalkylation catalyst in said first reaction zone.

9. The process of claim 1, wherein the transalkylation catalyst and the alkylation catalyst comprise different aluminosilicate molecular sieves wherein the transalkylation catalyst has a pore size greater than that of the alkylation catalyst.

10. The process of claim 1, wherein said alkylation catalyst comprises a molecular sieve of the MCM-22 family selected from the group consisting of MCM-22, PSH-3, SSZ-25, ERB-1, ITQ-1, ITQ-2, ITQ-30, MCM-36, MCM-49, MCM-56, UZM-8 and mixtures thereof.

11. The process of claim 1, wherein said conditions in said first reaction zone during said contacting (c) are such as to maintain said polyalkylated aromatic compound and said alkylatable aromatic compound substantially in the liquid phase.

12. The process of claim 1, wherein said conditions in said first reaction zone during said contacting (c) comprise a temperature between about 50° C. and about 300° C. and a pressure between about 170 kPa and about 10,000 kPa.

13. The process of claim 1, wherein said conditions in said second reaction zone during said contacting (h) are such as to maintain said alkylatable aromatic compound substantially in the liquid phase.

14. The process of claim 1, wherein said conditions in said second reaction zone during said contacting (h) comprise a temperature between about 50° C. and about 270° C. and a pressure between about 1,000 kPa and about 10,000 kPa.

15. The process of claim 1, wherein said alkylatable aromatic compound comprises benzene or naphthalene.

16. The method of claim 1, wherein said alkylating agent comprises at least one of ethylene, propylene, 1-butene, 2-butene, and isobutylene.

* * * * *